(12) United States Patent
Nolan et al.

(10) Patent No.: US 9,120,711 B2
(45) Date of Patent: Sep. 1, 2015

(54) CARBOXYLATION CATALYSTS

(75) Inventors: Steven P. Nolan, St Andrews (GB); Catherine Cazin, St Andrews (GB)

(73) Assignee: University Court of the University of St. Andrews, St. Andrews (GB)

( * ) Notice: Subject to any disclaimer, the term of this patent is extended or adjusted under 35 U.S.C. 154(b) by 53 days.

(21) Appl. No.: 13/702,886

(22) PCT Filed: Jun. 9, 2011

(86) PCT No.: PCT/GB2011/000868
§ 371 (c)(1),
(2), (4) Date: Dec. 7, 2012

(87) PCT Pub. No.: WO2011/154700
PCT Pub. Date: Dec. 15, 2011

(65) Prior Publication Data
US 2013/0085276 A1 Apr. 4, 2013

(30) Foreign Application Priority Data

Jun. 9, 2010 (GB) .................................. 1009656.8

(51) Int. Cl.
| | |
|---|---|
| *C07B 41/08* | (2006.01) |
| *C07D 233/02* | (2006.01) |
| *C07D 233/04* | (2006.01) |
| *C07D 233/90* | (2006.01) |
| *C07D 207/04* | (2006.01) |
| *C07D 207/18* | (2006.01) |
| *B01J 23/66* | (2006.01) |
| *B01J 23/72* | (2006.01) |
| *B01J 31/22* | (2006.01) |
| *B01J 31/18* | (2006.01) |
| *B01J 31/24* | (2006.01) |
| *C07B 59/00* | (2006.01) |
| *C07D 235/24* | (2006.01) |
| *C07D 237/24* | (2006.01) |
| *C07D 249/10* | (2006.01) |
| *C07D 253/07* | (2006.01) |
| *C07D 261/18* | (2006.01) |
| *C07D 263/34* | (2006.01) |
| *C07D 263/58* | (2006.01) |
| *C07D 275/03* | (2006.01) |
| *C07D 277/56* | (2006.01) |
| *C07D 277/68* | (2006.01) |
| *C07D 307/68* | (2006.01) |
| *C07D 473/00* | (2006.01) |
| *C07F 1/08* | (2006.01) |
| *C07F 1/10* | (2006.01) |

(52) U.S. Cl.
CPC ............... *C07B 41/08* (2013.01); *B01J 31/185* (2013.01); *B01J 31/2226* (2013.01); *B01J 31/2265* (2013.01); *B01J 31/2269* (2013.01); *B01J 31/2273* (2013.01); *B01J 31/24* (2013.01); *C07B 59/002* (2013.01); *C07D 233/90* (2013.01); *C07D 235/24* (2013.01); *C07D 237/24* (2013.01); *C07D 249/10* (2013.01); *C07D 253/07* (2013.01); *C07D 261/18* (2013.01); *C07D 263/34* (2013.01); *C07D 263/58* (2013.01); *C07D 275/03* (2013.01); *C07D 277/56* (2013.01); *C07D 277/68* (2013.01); *C07D 307/68* (2013.01); *C07D 473/00* (2013.01); *C07F 1/08* (2013.01); *C07F 1/10* (2013.01); *B01J 2531/16* (2013.01); *B01J 2531/17* (2013.01); *B01J 2531/18* (2013.01)

(58) Field of Classification Search
CPC .. C07D 233/02; C07D 233/04; C07D 233/90; C07D 207/04; C07D 207/18; C07B 41/08; B01J 31/2269; B01J 31/2273; B01J 2531/16; B01J 2531/17; B01J 2531/18; B01J 23/66; B01J 23/72
USPC ............. 548/101; 556/21, 110; 502/152, 162; 560/8
See application file for complete search history.

(56) References Cited

U.S. PATENT DOCUMENTS

2007/0240797 A1 10/2007 Mendenhall et al.
2009/0018330 A1* 1/2009 Molt et al. ...................... 544/64

OTHER PUBLICATIONS

European Patent Office, PCT International Search Report and Written Opinion of International Searching Authority for International Application No. PCT/GB2011/000868 dated Aug. 19, 2011.
Acevedo-Chavez, Rodolfo, et al., Transition metal compounds of the purinic isomer allopurinol. Part 1, Transition Metal Chemistry 15(6), 434-438 (1990) and abstract.
Acevedo-Chavez, Rodolfo, et al., Antiferromagnetic coupling in the cyclic octanuclear compound [Cu(II) (micro-3,5-dimethylpyrazolate)(micro-OH)] and its Analogue [Cu(II)(micro-pyrozolate)(micro-OH)], Journal of Solid State Chemistry 132, 24-32 (1997) and abstract.

(Continued)

*Primary Examiner* — Venkataraman Balasubramanian
(74) *Attorney, Agent, or Firm* — Christopher J. Knors; Moore & Van Allen, PLLC

(57) ABSTRACT

The use of a complex of the form Z—M—OR in the carboxylation of a substrate is described. The group Z is a two-electron donor ligand, M is a metal and OR is selected from the group consisting of OH, alkoxy and aryloxy. The substrate may be carboxylated at a C—H or N—H bond. The metal M may be copper, silver or gold. The two-electron donor ligand may be a phosphine, a carbene or a phosphite ligand. Also described are methods of manufacture of the complexes and methods for preparing isotopically labelled caboxylic acids and carboxylic acid derivatives.

16 Claims, No Drawings

(56) References Cited

OTHER PUBLICATIONS

Ainscough, Eric W., et al, The interaction of 1-methylimidazoline-2(3H)-thione with copper (II) salts, Journal of the Chemical Society Dalton Transactions: Inorganic Chemistry, 1, 39-42 (1989) and abstract.

Aoki, Massao, et al., Bidentate amidine ligands for nickel(0)-mediated coupling of carbon dioxide with unsaturated hydrocarbon, Chem. Commun., 2568-2569 (2004).

Aresta, Michele, Carbon Dioxide Recovery and Utilization, Kluwer Academic Publishers. Dordrecht, The Netherlands, 210-277, 394-402 (2003).

Bonet, Amadeu, et al., The selective catalytic formation of beta-boryl aldehydes through a base-free approach, Org. Biomol. Chem., 7, 1533-1535 (2009).

Boogaerts, Ine I.F., et al., Carboxylation of C-H Bonds Using N-Heterocyclic Carbene Gold(I) Complexes, J. Am. Chem. Soc., 132, 8858-8859 (2010).

Boogaerts, Ine I.F., et al., Carboxylation of N-H/C-H Bonds Using N-Heterocyclic Carbene Copper(I) Complexes, Angew. Chem. 122, 8856-8859 (2010).

De Fremont, Pierre, et al., Synthesis of Well-Defined N-Heterocyclic Carbene Silver(I) Complexes, Organometallics, 24, 6301-6309 (2005).

Demember, John R., et al, Silver(I) Chemistry in Aqueous Alkaline Media. 2. Study of the Interaction of Silver(I) with beta-Disulfone Carbanions in Aqueous Alkaline Media, J. Am. Chem. Soc., 105(17), 5647-5652 (1983) and abstract.

Dupuy, Stephanie, et al., Decarboxylation of aromatic carboxylic acids by gold(I)-N-heterocyclic carbine (NHC) complexes, Chem. Commun. 47, 5455-5457 (2011).

Fortman, George C., et al., A Versatile Cuprous Synthon:[Cu(IPr)(OH)](1Pr=1,3 bis(diisopropylphenyl) imidazol-2-ylidene), Organometallics, 29, 2966-3972 (2010).

Franks, Russell J., et al., Palladium-Catalyzed Carboxylative Coupling of Allylstannanes and Allyl Halides, Organometallics, 19, 1458-1460 (2000).

Gaillard, Sylvain, et al., A N-heterocyclic carbene gold hydroxide complex: a golden synthon, Chem. Commun., 46, 2742-2744 (2010).

Hamashima, Yoshitaka, et al., Catalytic Enantioselective Fluorination of Oxindoles, J. Am. Chem. Soc., 127, 10164-10165 (2005).

Jessop, Philip G., et al., Recent advances in the homogeneous hydrogenation of carbon dioxide, Coordination Chemistry Reviews, 248, 2425-2442 (2004).

Johansson, Roger, et al, Insertion of CO2 into a palladium allyl bond and a Pd(II) catalysed carboxylation of allyl stannanes, Dalton Trans., 488-492 (2007).

Jurkauskas, Valdas, et al, Conjugate Reduction of alpha,beta-Unsaturated Carbonyl Compounds Catalyzed by a Copper Carbene Complex, Organic Letters, 5(14), 2417-2420 (2003).

Kaur, Harneet, et al, (NHC)CU(NHC=N-Heterocyclic Carbene) Complexes as Efficient Catalysts for the Reduction of Carbonyl Compounds, Organometallics, 23, 1157-1160 (2004).

Kissner, Reinhard, et al., The Hydrolysis of gold(I) in aqueous acetonitrile solutions, J. Chem. Soc., Dalton Trans., 1773-1777 (1997) and abstract.

Mankad, Neal P., et al, Synthesis, Structure, and CO2 Reactivity of a Two-Coordinate (Carbene)copper(I) Methyl Complex, Organometallics, 23, 1191-1193 (2004) and abstract.

Marion, Nicolas, et al, [(NHC)Au]-Catalyzed Formation of Conjugated Enones and Enals: An Experimental and Computational Study, Chem. Eur. J., 13, 6437-6451 (2007).

Muthu, Sebastian, et al., Coordination networks of Ag(I) and N,N'-bis(3-pyridine-carboxamide)-1,6-hexane: structures and anion exchange, J. Chem. Soc., Dalton Trans., 4561-4568 (2002).

Nemoto, Koji, et al., Carboxylation of indoles and pyrroles with CO2 in the presence of dialkylaluminum halides, Tetrahedron Letters 50, 4512-4514 (2009).

Olah, George A., et al., Efficient Chemoselective Carboxylation of Aromatics to Arylcarboxylic Acids with a Superelectrophilically Activated Carbon Dioxide—Al2Cl5/Al System, J. Am. Chem. Soc., 124, 11379-11391 (2002).

Papal, Imre, et al., Mechanistic Details of Nickel(0)-Assisted Oxidative Coupling of CO2 with C2H4, Organometallics, 23, 5252-5259 (2004)>.

Park, Chul Min, et al., Synthesis and structure-activity relationship of 1H-indole-3-carboxylic acid pyridine-3-ylamides: A novel series of 5-HT2c receptor antagonists, Bioorganic & Medicinal Chemistry Letters, 18, 3844-3847 (2008).

Pyykkoe, Pekka, et al., Theory of the d10-d10 Closed-Shell Attraction 4. X(AuL)nm+ Centered Systems, Organometallics, 17, 4842-4852 (1998) and abstract.

Qiu, Yong-Qing, et al., Quantum chemistry calculation on structures and NLO coefficients of H3PauR type mononucleaus Au(I) complex, Inst. Functional Meter. Chem. Fac. Chem., Northeast Normal Univ., Gaodeng Xuexiao Huaxue Xuebao,27(9),1703-1707 (2006).

Rajeswaran, Walajapet G., et al., Studies on Protection of Oxindoles, Tetrahedron, 54, 11375-11380 (1998).

Saito, Shinichi, et al., Nickel-Mediated Regio- and Chemoselective Carboxylation of Alkynes in the Presence of Carbon Dioxide, J. Org. Chem. 64, 3975-3978 (1999).

Sakakura, Toshiyasu, et al., Transformation of Carbon Dioxide, Chem. Rev., 107, 2365-2387 (2007).

Takimoto, Masanori, et al., Highly Enantioselective Catalytic Carbon Dioxide Incorporation Reaction: Nickel-Catalyzed Asymmetric Carboxylative Cyclization of Bis-1,3-dienes, J. Am. Chem. Soc., 126, 5956-5957 (2004).

Ukai, Kazutoshi, et al., Rhodium(I)-Catalyzed Carboxylation of Aryl- and Alkenylboronic Esters with CO2, J. Am. Chem. Soc., 128, 8706-8707 (2006).

Yeung, Charles S., et al., Beyond Aresta's Complex: Ni- and Pd-Catalyzed Organozinc Coupling with CO2, J. Am. Chem. Soc., 130, 7826-7827 (2008).

European Patentoffice, PCT International Search Report and Written Opinion of the International Searching Authority for International ApplicationNo. PCT/GB2011/000868 date of completion Aug. 9, 2011.

GB Intellecutal Property Office, GB Search Report for GB ApplicationNo. GB1009656.8 dated Oct. 11, 2010.

North, Michael, Synthesis of beta,gamma-Unsaturated Acids from Allenes and Carbon Dioxide, Angew. Chem. Int. Ed., 48, 4104-4105 (2009).

Correa, Arkaitz, et al., Palladium-Catalyzed Direct Carboxylation of Aryl Bromides with Carbon Dioxide, J. Am. Chem. Soc., 131, 15974-15975 (2009).

Japanese Patent Office, Japanese Patent Application No. 2013-513744, Office Action dated Feb. 10, 2015, 4 pages.

Li Dang et al., "DFTStudies on the Carboxylation of Arylboronate Esters with CO2 Catalyzed by Copper(I) Complexes," American Chemical Society 2010, Jan. 26, 2010, pp. 2-12.

Takeshi Ohishi et al., "Carboxylation of Organoboronic Esters Catalyzed by N-Hereocyclic Carbene Copper(I) Complexes." Angewandte Chemie, International Edition, 2008, 47(31), pp. 5792-5795.

Citadelle et al., "Simple and Versatile Synthesis of Copper and Silver N-Heterocyclic Carbene Complexes in Water or Organic Solvents," The Royal Society of Chemistry 2010, Apr. 19, 2010, Dalton Trans., 2010,39, pp. 4489-4491.

* cited by examiner

CARBOXYLATION CATALYSTS

CROSS-REFERENCE TO RELATED APPLICATIONS

This application is filed under the provisions of 35 U.S.C. §371 and claims the benefit of International Patent Application No. PCT/GB2011/000868, filed on Jun. 9, 2011, entitled "CARBOXYLATION CATALYSTS", which claims the benefit of priority of GB Application No. 1009656.8, filed on Jun. 9, 2010, the contents of both of which are hereby incorporated by reference herein in their entirety.

FIELD OF THE INVENTION

The present invention relates to the use of metal hydroxide, alkoxide and aryloxide complexes in carboxylation reactions, in particular in the functionalisation of C—H and N—H bonds to produce carboxyl containing compounds.

BACKGROUND TO THE INVENTION

Carbon dioxide ($CO_2$) is considered an abundant and renewable C1 source, thus transition-metal mediated activation of this thermodynamically and kinetically stable molecule has received much attention over the last decade.[1] In this context, C—C bond formation reactions simply involving $CO_2$ and a unique metal center with allyl halides, alkenes, alkynes and allenes have been achieved, although with limited functional group compatibility.[2-4,5]

In addition transition-metal mediated carbonylation of heterocyclic N—H and C—H bonds represents a nascent area in organic chemistry, enabling efficient construction of valuable synthons.[1] Palladium-catalysed N-carbonylation is well-documented, but requires high catalyst loading and the utility of either gaseous carbon monoxide or Group VI metal-carbonyl complexes.[2] This transformation is also promoted by molybdenum and tungsten carbonyl amine species under forcing temperatures.[3] Several successful approaches to C-carbonylation have been reported using ruthenium[1a] and nickel catalysts,[4] however examples under mild conditions remain elusive. Moreover, substrate scope is limited to arenes that are either electron-rich or bear synthetically restricting directing groups, and the product is often recovered as a regioisomeric mixture.

There is therefore a need to find alternative means of adding carbon as a C1 unit to a substrate in synthetic chemistry, for example in the form of $CO_2$.

DESCRIPTION OF THE INVENTION

According to a first aspect the present invention provides the use of a complex of the form Z—M—OR in the carboxylation of a substrate; wherein
  the group Z is a two-electron donor ligand;
  M is a metal; and
  OR is selected from the group consisting of OH, alkoxy and aryloxy.

The substrate may be carboxylated at a C—H or N—H bond. Typically the substrate is carboxylated at the most acidic C—H or N—H bond. The substrate may be a substituted or unsubstituted aromatic compound, for example a substituted or unsubstituted heteroaraomatic compound. Examples of substrates that may be carboxylated include five or six membered aromatic and heteroaromatic rings. Specific examples of such substrates are described hereafter.

Where —OR is alkoxy the group R may be a primary, secondary or tertiary alkyl group (for example C1-C10 or even C1-C4 alkyl groups) that may be substituted or unsubstituted and may be unsaturated. Cycloalkyl groups R may also be employed, for example five or six membered rings or even bicyclic groups. Cycloalkyl groups R may be substituted or unsubstituted and may be unsaturated. Where —OR is aryloxy the group R may be substituted or unsubstituted phenyl, substituted or unsubstituted naphthyl, or substituted or unsubstituted anthracenyl, or a substituted or unsubstituted heterocycle.

The metal M may be copper, silver or gold.

The two-electron donor ligand may be, for example a phosphine, a carbene or a phosphite ligand.

Complexes Z—M—OR have been found to be capable of carboxylation of a range of substrates containing C—H or N—H bonds using carbon dioxide itself as the source of —$CO_2$. Moderate temperatures and pressures may be employed. For example the temperature may be from 0 to 100° C. For example a $CO_2$ pressure of from 1 to 10 bars may be employed. It will be appreciated that higher or lower temperatures and pressures may be required or desirable and that suitable conditions for reaction can be readily determined.

Thus the present invention provides a process for the production of a carboxylic acid, carboxylate salt or carboxylic acid derivative comprising:
reacting carbon dioxide with a substrate containing at least one C—H or N—H bond in the presence of a complex of the form Z—M—OR as described herein.

The reaction is carried out in the presence of a suitable base, for example a metal hydroxide such as NaOH, KOH or CsOH. Alternatively an alkali metal alkoxide base may be employed.

The carboxylate derivatives can include esters, prepared as described hereafter, for example. Other carboxylate derivatives such as amides may also be produced by making use of the methods of the invention.

In the carboxylation processes of the invention the complexes Z—M—OR can act as catalysts in relatively simple and convenient procedures as described hereafter in more detail with reference to specific examples. The invention can provide straightforward and economic methods utilising $CO_2$ to functionalise C—H or N—H bonds to produce carboxyl containing compounds. Thus the present invention provides the use of complexes of the form Z—M—OR as catalysts in the carboxylation of a substrate, for example a substrate containing at least one C—H or N—H bond.

The two electron donor ligand Z may be of several different forms.

Examples of phosphine ligands include those of the form $PR_3$ wherein each R group may be the same or different and may be alkyl, aryl, cyclic or heterocyclic. All of these groups may be substituted or unsubstituted, saturated or unsaturated. Where the group R is cyclic or heterocyclic it may be aromatic.

Advantageously the phosphine ligand may be triphenylphosphine or substituted triphenylphenylphosphine. For example: tris(2-tolyl)phosphine and tris(2-MeO-phenyl)phosphine and tris(2,4-di-tert-butylphenyl)phosphine.

Examples of phosphite ligands include those of the form $P(OR)_3$ wherein each OR group may be the same or different and R may be alkyl, aryl, cyclic or heterocyclic. All of these groups may be substituted or unsubstituted, saturated or unsaturated. Where the group R is cyclic or heterocyclic it may be aromatic.

Advantageously the phosphite groups may be triphenylphosphite or substituted triphenyl phosphite, typically bearing sterically demanding substituents, for example: tris (2-tolyl)phosphite and tris(2-MeO-phenyl)phosphite and tris (2,4-di-tert-butylphenyl)phosphite.

Examples of carbene ligands include cyclic or acyclic carbenes having one or more heteroatoms. The heteroatom (or heteroatoms) may be the same or different and may be N, O or S for example. The presence of such heteroatoms stabilises the carbene ligand.

Advantageously a carbene ligand is a heterocyclic carbene ligand, especially a nitrogen containing heterocyclic carbene ligand (NHC). The NHC may have a five or six membered ring, typically a five membered ring. N-heterocyclic carbene ligands (NHC ligands) have been shown to provide good stabilising effects for reactive intermediates and their use in organometallic chemistry, catalysis and medicine is increasing (5,6).

The NHC employed in the complexes may be saturated or unsaturated and may contain one or more nitrogen atoms an optionally may contain other heteroatoms (such as O and S) in the ring.

For example the ligand may have the form

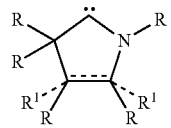

wherein the groups R may be the same or different, the groups $R^1$ where present may be the same or different and the dashed line in the ring represents optional unsaturation. One or more of the carbon atoms in the ring (apart from the carbene carbon) may be substituted with O or S. Each R and $R^1$ may be, independently for each occurrence, selected from: H, a primary or secondary alkyl group (for example C1-C10 or even C1-C4) that may be substituted or unsubstituted, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy;

Advantageously NHC ligands bearing two nitrogen atoms in the ring, each adjacent the carbene carbon may be employed. The NHC carbene ligands of this type may have the form:

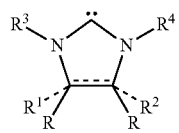

wherein each of the groups R, $R^1$ $R^2$, $R^3$ and $R^4$ may be the same or different and the dashed line in the ring represents optional unsaturation, wherein $R^1$ and $R^2$ are absent. Each R and $R^1$, $R^2$, $R^3$ and $R^4$ may be, independently for each occurrence, selected from: H, a primary or secondary alkyl group (for example C1-C10 or even C1-C4) that may be substituted or unsubstituted, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy.

Advantageously the groups $R^3$ and $R^4$ may be substituted or unsubstituted aromatic rings that may be heterocyclic aromatic rings. Substituents R, $R^1$ $R^2$, $R^3$ and $R^4$ in the structures above may include alkyl and unsaturated alkyl groups, aryl groups that may be substituted and may contain heteroatoms.

Suitable examples of NHC carbene ligands include those according to formulas I to IV below:

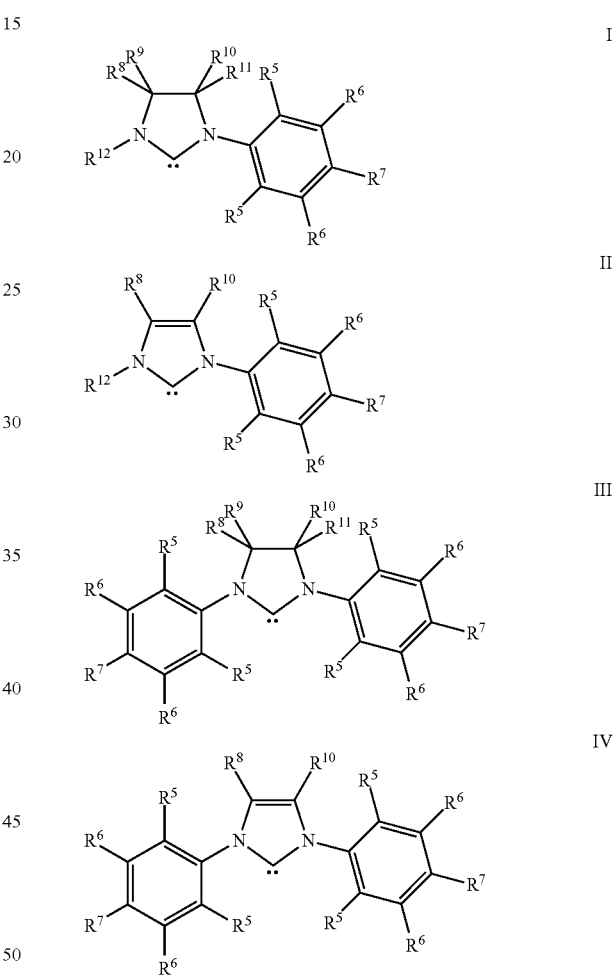

Wherein each group $R^5$, $R^6$ and $R^7$, is independently for each occurrence selected from: H, a primary or secondary alkyl group (for example C1-C10 or even C1-C4) that may be substituted or unsubstituted, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; $R^8$, $R^9$, $R^{10}$ and $R^{11}$ are each independently for each occurrence H, a substituted or unsubstituted alkyl group (for example C1-C10 or even C1-C4), substituted or unsubstituted aryl, or in formulas (II) and (IV) together with the carbons carrying them form a substituted or unsubstituted, fused 4-8 membered carbocylic ring or a substituted or unsubstituted, fused aromatic ring, preferably a fused phenyl ring; and $R^{12}$ is alkyl (for example C1-C10 or even C1-C4) or a cycloalkyl (for example C3-C8).

For example these NHC carbenes

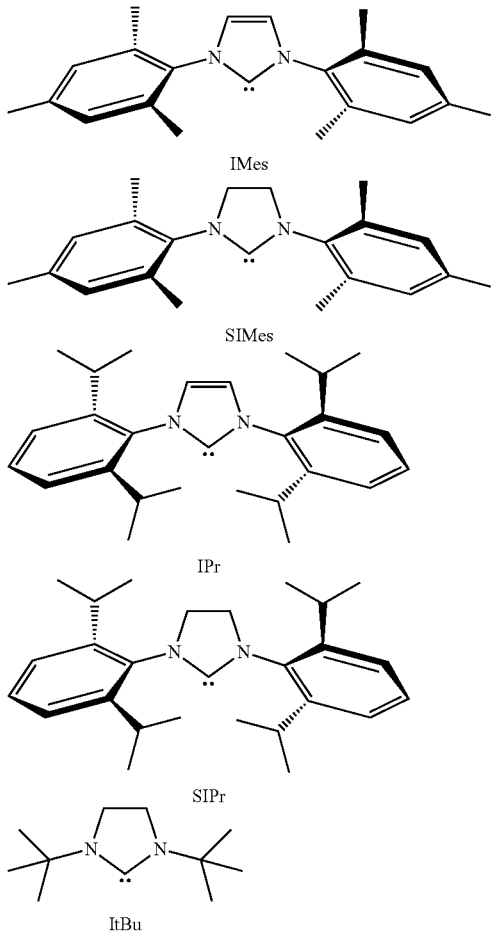

are suitable examples of the NHC carbene family for the formation of the complexes, the alkyl substituted aromatic rings providing additional stabilisation to the carbene tone pair of electrons.

Examples of suitable complexes of the form Z—M—OR include gold hydroxide complexes NHC—Au—OH such as those disclosed in reference 6—("A N-Heterocyclic Carbene Gold Hydroxide Complex: A Golden Synthon" Gaillard, S.; Slawin, A. M. Z.; Nolan, S. P. Chem. Commun. 2010, 46, 2742-2744). Similar copper hydroxide complexes NHC—Cu—OH have not been described before but can be prepared by a route analogous to that described in reference 6, for example reaction of a chloride complex of the form NHC—Cu—Cl with a base such as CsOH to give NHC—Cu—OH. Similar silver hydroxide complexes NHC—Ag—OH can also be prepared in a similar fashion. Like the corresponding gold hydroxide complexes, these copper and silver hydroxide complexes can therefore find use as catalysts in the carboxylation processes described herein or for other processes, for example where their basicity is sufficient to abstract a proton from a substrate.

Complexes of the form NHC—Cu—X, where X is halogen, such as Cl, are described, for example, in references 7 (Jurkauskas, V.; Sadighi, J. P.; Buchwald, S. L. Conjugated Reduction of α,β-Unsaturated Carbonyl Compounds Catalyzed by a Copper Carbene Complex. Org. Lett. 2003, 5, 2417-2420) and 8 (Kaur, H.; Zinn, F. K.; Stevens, E. D.; Nolan, S. P. (NHC)CuI (NHC=N-Heterocyclic Carbene) Complexes as Efficient. Catalysts for the Reduction of Carbonyl Compounds. Organometallics 2004, 23, 1157-1160). Silver complexes NHC—Ag—X are also known from reference 14 (de Frémont, P.; Scott, N. M.; Stevens, E. D.; Ramnial, T.; Lightbody, O. C.; Macdonald, C. L. B.; Clyburne, J. A. C.; Abernethy, C. D.; Nolan, S. P. Synthesis of Well-Defined N-Heterocyclic Carbene Silver (I) Complexes. Organometallics, 2005, 24, 6301-6309).

Examples of copper, silver or gold hydroxide complexes include where Z is one of the NHC groups: IMes, SIMes, IPr, ItBu or SIPr. Thus suitable complexes for carrying out the methods described herein include:

[M(OH)(IMes)], [M(OH)(SIMes)], [M(OH)(IPr)], [M(OH)(ItBu)], and [M(OH)(SIPr)], where M can be Au, Ag or Cu.

In general the complexes of the form Z—M—OR, where Z,M and OR are as described before may be prepared by substitution of X in a complex of the form Z—M—X, or in a salt of the form Z—M$^+$ X$^-$, wherein X is a suitable anion or anionic ligand, for example halide or pseudohalide. Suitable groups X thus include, halide, carboxylate, alkoxy, aryloxy, alkylsulfonate, acetate, trifluoroacetate, tetrafluroborate, hexafluorophosphate, hexafluoroantimonate, cyanide, thiocyanates, isothiocyanates, cyanates, isocyanates, azides and selenocyanates.

For example the hydroxide complexes and other complexes of the invention can be made from a corresponding complex of the form [M(X)(NHC)] where X is a suitable leaving group such as a halide, for example chloride, bromide or iodide. Reaction with a suitable hydroxide forms the hydroxide complex and reaction with an alkoxide or aryloxide can form corresponding complexes where R in Z—M—OR is alkyl or aryl.

Where the group OR is not hydroxyl, i.e. R is alkyl or aryl; gold, silver and copper complexes of the form Z—M—OR may also be made by reaction of the corresponding hydroxide complex with the appropriate alcohol thus:

Z—M—OH+HOR→Z—M—OR+H$_2$O

Thus according to another aspect the present invention provides a copper or silver complex of the form Z—Cu—OR wherein the group Z is a two-electron donor ligand as described before and the group OR is selected from the group consisting of hydroxyl alkoxy and aryloxy as described before.

Thus according to yet another aspect the present invention provides a method of manufacture of a copper or silver complex of the form Z—M—OR as described above, the method comprising:

reacting a copper (I) or silver complex of the form Z—M—X or a salt of the form Z—M$^+$ X$^-$, wherein M is copper or silver, Z is a two-electron donor ligand as described before and X is an anionic ligand or an anion; with an alkali metal hydroxide, alkoxide or aryloxide.

X may be selected from halide, carboxylate, alkoxy, aryloxy, alkylsulfonate, acetate, trifluoroacetate, tetrafluroborate, hexafluorophosphate, hexafluoroantimonate, cyanide, thiocyanates, isothiocyanates, cyanates, isocyanates, azides and selenocyanates. The corresponding gold complexes may be made in similar fashion.

Some copper alkoxide and aryloxide complexes are known as described in reference 12 (N. P. Mankad, T. G. Gray, D. S. Laitar, J. P. Sadighi, Organometallics 2004, 23, 1191).

Alternatively and according to yet another aspect the present invention provides a method of manufacture of a metal complex of the form Z—M—OR wherein OR is alkoxide or aryloxide as described above, the method comprising: reacting a complex of the form Z—M—OH, wherein M is copper, silver or gold and Z is a two-electron donor ligand as described before; with a compound of the formula HOR wherein OR is alkoxy or aryloxy as described above.

The complexes Z—M—OR may be generated in situ. For example, with a complex of the form [M(X)(NHC)], or a salt [M(NHC)⁺X⁻], addition of a hydroxide base to a reaction mixture will generate [M(OH)(NHC)] as described hereafter with reference to specific examples.

The methods of the invention can be used to carboxylate a wide range of substrates, some examples of which are described in more detail hereafter.

In a typical procedure a substrate having at least one C—H or N—H bond is reacted with gaseous $CO_2$ in a presence of a complex of the form Z—M—OR and a base in a suitable solvent. Suitable solvents can include but are not limited to THF, toluene, methanol, diethyl ether. After reaction a carboxylic acid, carboxylate salt or carboxylate derivative, such as an ester can be isolated, depending on the work up procedure or the use of additional reaction steps. For example oxazole can be converted in high yield (more than 90%) to the corresponding carboxylic acid as shown in Scheme 1 below:

Scheme 1

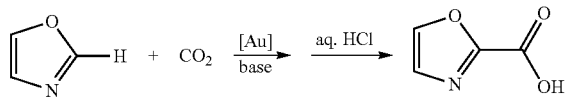

where [Au] is a gold hydroxide complex such as [(IPr)AuOH]. The base may be KOH and the reaction may be carried out in THF before quenching/neutralisation with aqueous HCl. Further examples of this reaction are given in the detailed description of the invention described hereafter. In such reactions the gold hydroxide complexes were shown to act as catalysts and it was also shown that the gold hydroxide complexes could be formed in situ from the corresponding gold chloride complex e.g. [(IPr)AuCl].

A wide range of other substrates, for example heterocycles or arenes can be carboxylated in this fashion. Further examples are provided hereafter.

Copper complexes have been shown to react similarly, for example 2-methylimidazole can be carboxylated on a nitrogen as shown in Scheme 2 below and the resultant carboxylate product isolated as the methyl ester by subsequent reaction with methyl iodide.

Scheme 2

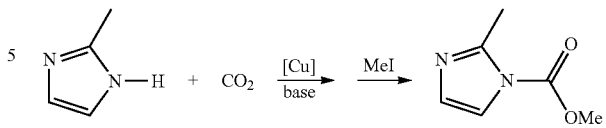

In Scheme 2 [Cu] is a copper hydroxide complex such as [(IPr)CuOH], the base may be KOH and the reaction may be carried out in THF before quenching with iodomethane to form the methyl ester of the carboxylic acid. As with the gold complex example of Scheme 1 the copper hydroxide complex functions catalytically and can be formed in situ, if desired, from a corresponding copper chloride complex e.g. [(IPr)CuCl], by the action of the base.

In general the carboxylation processes of the present invention provide carboxylation at the most acidic H on the substrate. Where a target C—H or N—H has a pKa below that of the complex Z—M—OR then reaction may be expected to occur. For example gold and copper hydroxide complexes described in more detail herein have pKa values in a range of the order of 27 to 32 and so can react with substrates having C—H or N—H with lower pKa.

A possible reaction mechanism was elucidated by carrying out the process stepwise and with stoichiometric rather than catalytic concentrations of a gold complex as shown in Scheme 3 below. An important feature of this transformation is the use of C—H and N—H bonds directly to lead to a metal species bearing both the NHC and the novel hydrocarbyl or heterocyclyl group by simple acid/base exchange and elimination of water. This process is made possible by the acidic nature of the reactant C—H or N—H bonds.

Thus according to another aspect the present invention provides a method of preparing complexes of the form Z—M—W, wherein Z is a two electron donor, M is copper, silver or gold and W is a substrate having N or C bonded to M; the method comprising:
  providing a complex of the form Z—M—OR, wherein Z is a two electron donor as described before, M is copper, silver or gold and OR is selected from the group consisting of OH, alkoxy and aryloxy; and
  reacting the complex Z—M—OR with a substrate comprising a C—H or N—H bond that is more acidic (has a lower pKa) than the M—OR bond of the complex.

Thus the processes to produce carboxylated substrates described herein may be carried out stepwise or in a single "one pot" catalytic fashion as desired.

Scheme 3

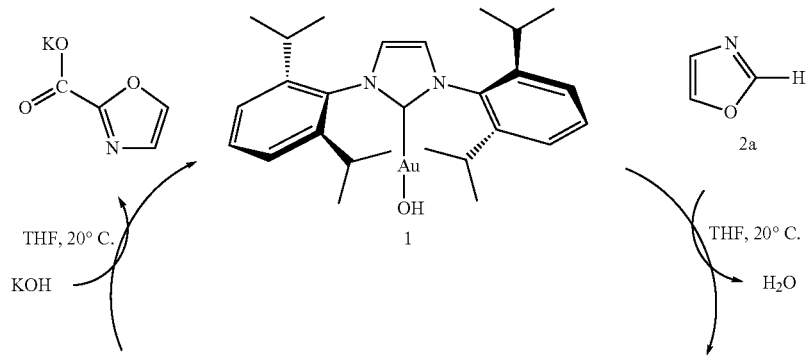

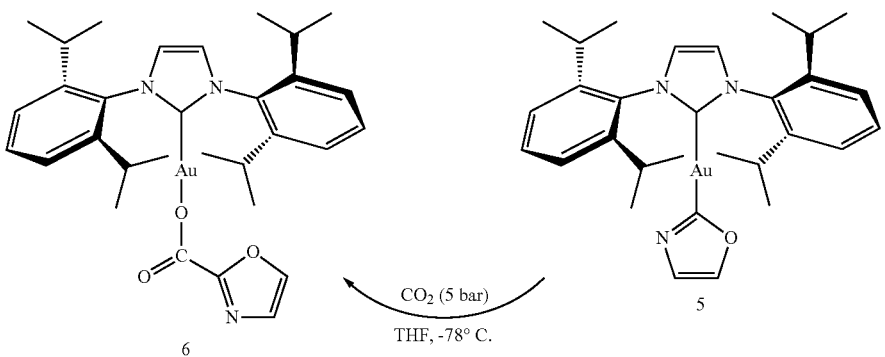

Reaction of [Au(OH)(IPr)] (1) with oxazole (2a) afforded the gold (I) oxazole species 5 in 93% isolated yield. A solution of 5 was saturated with CO₂ at −100° C. to afford the carboxylate complex 6 which was isolated in 86% yield. Reaction of 6 with KOH (1 equivalent) resulted in precipitation of potassium oxazole-2-carboxylate. Thus it can be seen that the base, KOH, regenerates the gold hydroxide complex 1 and releases the carboxylate salt product from intermediate 6.

When reaction is carried out with the substrate 2a, $CO_2$, KOH and gold hydroxide complex 1 all present together, the complete cycle shown in Scheme 3 operates. Thus the gold hydroxide complex 1 functions as a catalyst and can be present in low concentration, for example at only 1.5 mol %, as it is regenerated continuously. With this approach isolated yields of carboxylic acid product in excess of 90% have been achieved.

The methods of the present invention tend to carboxylate at the most acidic C—H or N—H position and are therefore selective. For example studies of the carboxylation of various oxazole derivatives resulted in carboxylation at the C2 position (on carbon adjacent the oxygen) rather than at the C3 position found using conventional acylation techniques. For example acylation of thiazole with [(IPr)AuCl] gave a 2.3:1 mixture of C2 and C5 carboxylated product—attributed to the fairly similar pKa of the C—H at these two positions. For example no product was formed using [(IPr)AuCl] ($pKa_{DMSO}$ of 30.3(2) for the hydroxide formed in situ) in reactions intended to carboxylate certain azole and pyrimidines compounds, but reaction with the more basic [(ItBu)AuCl] ($pKa_{DMSO}$ of 32.4(2) for the hydroxide formed in situ) was successful in caboxylating these less acidic compounds as described hereafter. In general the methods of the present invention show a high regioselectivity.

It has also been found that carboxylated species such as 6 in scheme 3 above may be decarboxylated thermally i.e. the reverse reaction to produce complexes such as 5 may occur.

For example the carboxylate addition products of gold complexes of the form Z—Au—OH and a wide range of aromatic and heteroaromatic carboxylic acids may be decarboxylated (reference 15) as shown in the general scheme below:

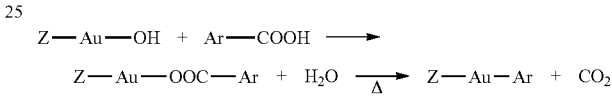

The reaction has also been found to be successful with non aromatic carboxylic acids and by making use of copper complexes. Typical solvents that may be employed for the decarboxylation include aromatic hydrocarbons such as toluene and ethers such as 1,4-dioxane.

Thus according to a yet further aspect the present invention provides a method for the preparation of a complex of general formula Z—M—$R^X$, wherein Z is a two electron donor ligand as described before, M is a metal that may be selected from gold, copper and silver; and $R^X$ is derived from a carboxylic acid of the form $R^X$—COOH. The method comprises reacting a complex of the form Z—M—OR as described before with a carboxylic acid of the form $R^X$—COOH to form a complex of the form Z—Au—OOC—$R^X$; and heating to decarboxylate. The carboxylic acid may be an alkyl, aromatic or heteroaromatic carboxylic acid that may be substituted or unsubstituted.

A yet further aspect of the present invention is in the preparation of isotopically labelled carboxylic acids, carboxylic acid salts and acid derivatives such as esters. The general method is outlined in Scheme 4 below with 1,5 dimethoxybenzoic acid (13) as the substrate and *CO₂ indicating isotopically labelled ($^{14}C$ or $^{13}C$) carbon dioxide. Carbon dioxide with isotopically labelled oxygen could also be employed.

Scheme 4

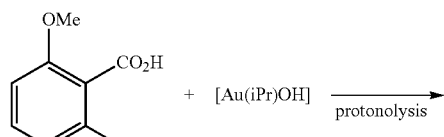

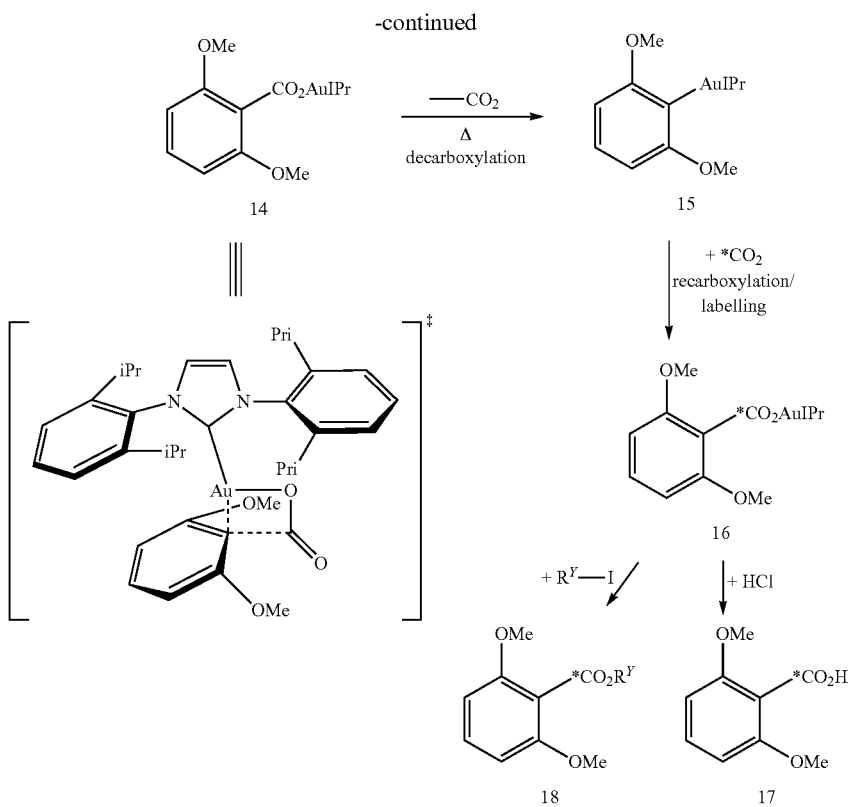

After formation of the gold adduct 14, thermal decarboxylation yields 15 which can be recarboxylated with labelled $CO_2$ to form 16 (for example using conditions similar to those shown in Scheme 3 above for the preparation of 6). The labelled carboxylic acid can be released from the gold by mineral acid to form labelled acid 17 or by alkyl or aryl halide (iodide, $R^Y$—I, shown in this example) to form an ester 18.

Thus the present invention provides a method of exchanging $CO_2$ on a carboxylic acid substrate to allow preparation of an isotopically labelled carboxylic acid or carboxylic acid derivative, the method comprising:

reacting a carboxylic acid of the general formula $R^X$—COOH with a complex of the form Z—M—OR as described before to form a complex of the form Z—M—OOC—$R^X$;

heating to form a complex of the form Z—M—$R^X$;

reacting the complex of the form Z—M—$R^X$ with isotopically labelled carbon dioxide to form an isotopically labelled complex of the form Z—M—OOC—$R^X$; and releasing the isotopically labelled isotopically carboxylic acid of the form $R^X$—COOH, or a corresponding carboxylic acid salt or carboxylic acid derivative from the complex Z—M—OOC—$R^X$. The carboxylic acid may be released from the complex by reaction with an acid such as a mineral acid or in the form of an ester by reaction with an organo halide.

In general complexes of the formula Z—M—$R^X$, even if —$R^X$ was not originally derived from reaction of $R^X$—COOH with a complex of the form Z—M—OR, may be carboxylated with a labelled carbon dioxide to provide a labelled carboxylic acid or carboxylic acid derivative. However the method described above is a convenient way of exchanging the carbon dioxide on an existing carboxylic acid, with a labelled carbon dioxide.

The group $R^X$— may be an alkyl, aromatic or heteroaromatic group that may be substituted or unsubstituted. For example the group $R^X$— may be a primary, secondary or tertiary alkyl group (for example C1-C10 or even C1-C4 alkyl groups) that may be substituted or unsubstituted and may be unsaturated. Cycloalkyl groups $R^X$— may also be employed, for example five or six membered rings or even bicyclic groups. Cycloalkyl groups $R^X$— may be substituted or unsubstituted and may be unsaturated. Where $R^X$— is aromatic the group $R^X$— may be substituted or unsubstituted phenyl, substituted or unsubstituted naphthyl, or substituted or unsubstituted anthracenyl, or a substituted or unsubstituted heterocycle.

When making an ester the organo halide may have halogen selected from Cl, Br and I. The group $R^Y$— shown in Scheme 4 above may be an alkyl, aromatic or heteroaromatic group such as discussed above in respect of $R^X$—. A carboxylic acid salt may be prepared by treatment with base or by releasing the corresponding carboxylic acid $R^X$—COOH from the complex Z—M—$R^X$ by use of an acid and then basifying the reaction mixture.

DESCRIPTION OF SOME PREFERRED EMBODIMENTS AND EXPERIMENTAL RESULTS

Gold Hydroxide Complexes

The formation of [Au(OH)(IPr)] was achieved by use of the reaction of $CsOH.H_2O$ with [Au(IPr)(Cl)] in dichloromethane at room temperature (88% isolated yield). More generally when in a 1:1 solution of THF and toluene for 24 hours at 60° C., both NaOH and KOH can also be used to produce high yields of [Au(OH)(IPr)] (92% and 92%, respectively) The same general methodology can be used to prepare other gold hydroxide complexes.

These complexes may also be obtained by treatment of the chloride complex (e.g. [Au(IPr)(Cl)] with a hydroxide in situ.

Copper Hydroxide Complexes

Copper hydroxide complexes can be made in similar fashion to the gold hydroxide complexes discussed above. For example [Cu(IPr)Cl] can be reacted with CsOH to produce [Cu(IPr)OH] as detailed below.

Synthesis of [Cu(IPr)(OH)]:

A 100 mL Schlenk tube was charged sequentially with [Cu(IPr)Cl] (250.0 mg, 0.51 mmol), dehydrated CsOH (18.0 mg, 0.12 mmol), toluene (20 mL) and THF (18 mL). The reaction mixture was stirred for 12 h at 60° C. The resultant orange solution was percolated through a short column of Celite and concentrated under reduced pressure until precipitation was observed. The product was crystallized by the slow addition of pentane (ca. 30 mL), collected on a glass frit in air and dried in vacuo to yield [Cu(IPr)(OH)] (132.0 mg, 55% yield) as a white microcrystalline solid. The product was recrystallized from THF/pentane under an inert atmosphere. IR (KBr): 3690, 3612, 3275, 3162, 3027, 2853, 1471, 1214, 1183, 1106, 1056, 938, 808, 764, 570, 548, 451. $^1$H NMR (CD$_2$Cl$_2$*, 300 MHz): δ7.56 (2H, t, $^2J_H$=7.8 Hz, Ar—CH), 7.35 (4H, d, $^2J_H$=7.8 Hz Ar—CH), 7.17 (2H, s, imid-CH), 2.60 (4H, sept., $^2J_H$=6.9 Hz, $^i$Pr—CH), 1.32 (12H, d, $^2J_H$=7.0 Hz, $^i$Pr—CH$_3$), 1.24 (12H, d, $^2J_H$=7.0 Hz, $^i$Pr—CH$_3$), −1.29 (1H, broad s, OH). $^{13}$C{$^1$H}NMR (CD$_2$Cl$_2$*, 75.5 MHz): δ182.3 (s, carbene C), 146.3 (s, Ar—C), 135.5 (s, Ar—C), 130.7 (s, imid-C), 124.6 (s, Ar—C), 123.6 (s, Ar—C), 29.2 (s, $^i$Pr—C), 25.0 (s, $^i$Pr—C), 24.1 (s, $^i$Pr—C). *Anal.* Calcd. for C$_{27}$H$_{37}$CuN$_2$O (MW 469.14): C, 69.12; H, 7.95; N, 5.97. Found: C, 69.32; H, 7.95; N, 5.99.

Silver Hydroxide Complexes

These may be made in similar fashion to the gold and copper complexes described above.

Metal Alkoxide/Aryloxide Complexes

These may be prepared from the complexes Z—M—X, by reaction with alkoxide or aryloxide as described before, or by displacement of hydroxide from Z—M—OH.

Example Synthesis of [Cu(IPr)(OR)](R=alkyl).

Typically 100 mg (0.213 mmol) of [Cu(IPr)OH] (1) was placed with 2 mL of toluene. One molar equivalent of ROH was added to the white suspension. Generally, dissolution of the complex occurred within minutes at which point the reaction was stirred for an addition 1 h. The solvent was subsequently stripped in vaccuo to approximately 0.75 mL at which point the product was precipitated from solution with the addition of pentane. The products were filtered from the solution and washed with pentane (3×3 mL) and dried under reduced pressure.

[Cu(IPr)(OMe)]

Reaction was left to stir for 14 h. White powder. 91% yield. Identity was confirmed by 1H NMR of previously reported preparation.[13]

[Cu(IPr)(O$^t$Bu)]

Reaction was left to stir for 14 h. White powder. 93% yield. Identity was confirmed by 1H NMR of previously reported preparation.[12]

Carboxylation Reactions—Gold Complexes

Carboxylation of oxazole with NHC-gold(I) catalysts.

The above reaction was carried out using gold hydroxide complexes [Au] as listed below in Table 1. In some examples (entries 6 to 9) the complex is generated in situ by the reaction of the base (KOH) with the corresponding chloride complex.

TABLE 1

| Entry | [Au] | Loading (mol %) | T (° C.) | TOF$^b$ (h$^{-1}$) | Yield$^c$ (%) |
|---|---|---|---|---|---|
| 1 | [(IPr)AuOH] (1) | 3.0 | 45 | 14.1 | 94 |
| 2 | 1 | 0 | 45 | 0 | 0 |
| 3 | 1 | 1.5 | 45 | 13.8 | 93 |
| 4 | 1 | 1.5 | 20 | 16.5 | 96 |
| 5 | 1 | 1.5 | 8 | 16.9 | 94 |
| 6 | [(IPr)AuCl] | 3.0 | 45 | 8.7 | 88 |
| 7 | [(IPr)AuCl] | 3.0 | 25 | 0.4 | 86 |
| 8 | [(IMes)AuCl] | 3.0 | 45 | n.d | 76 |
| 9 | [(I$^t$Bu)AuCl] | 3.0 | 45 | n.d | 68 |

$^a$Conditions: 1 mmol of 2a, 1.05 mmol of KOH, pCO$_2$ = 1.5 bar, 5 mL of THF, t = 12 h.
$^b$Turnover frequency determined after 2 hours, defined as mol of acid per mol of Au per hour.
$^c$Yield of isolated product.

IPr

IMes

I$^t$Bu

The strongly basic [(IPr)AuOH] (1) (IPr=1,3-bis(diisopropyl)phenylimidazol-2-ylidene) species has a $pKa_{DMSO}$ of 30.3 as determined by potentiometric titrimetry. Oxazole has a $pKa_{DMSO}$ of 27.1, therefore complex 1 is sufficiently basic to remove the oxazole C2 proton.

Table 1 shows reaction of oxazole (2a), ($pKa_{DMSO}$=27.1) with $CO_2$ using isolated [(NHC)AuOH] complexes and complexes generated in situ. In the presence of 3 mol % 1 and 1.05 mmol KOH in THF at 45° C., treatment of 2a (1 mmol) with $CO_2$ (1.5 bar) and subsequent acid hydrolysis afforded oxazole 2-carboxylic acid (3a) in quantitative yield (Table 1, entry 1). Carboxylation did not take place in the absence of either [(IPr)AuOH] or KOH under otherwise identical conditions.

Further testing revealed that catalyst loading could be reduced to 1.5 mol %, with higher turnover frequencies at lower temperatures, an observation that correlates with increased solubility of $CO_2$ (Table 1, entries 3-5). The [(IPr)Au] species generated in situ from [(IPr)AuCl] and KOH also demonstrated activity for the carboxylation of 2a, but profiles of $CO_2$ consumption versus time clearly show the existence of a significant induction period at lower temperatures (Table 1, entries 6 and 7). The presence of alternative NHC ligands led to lower yields of 3a (Table 1, entries 8 and 9).

Catalyst recycling experiments were carried out using [(IPr)AuOH] (1). Aqueous extraction of the catalyst solution at 45° C. allowed recovery of potassium oxazole 2-carboxylate and efficient recycling of [(IPr)AuOH] in the organic phase. A single aliquot of the catalyst solution could be recycled six times with 98% activity retention per cycle, giving a cumulative turnover number of 78.1 mol per mol of catalyst.

A number of other aromatic heterocycles were subjected to carboxylation catalysis under optimised catalytic conditions using [(IPr)AuOH] (1) as an example. Gold(I) mediated C—H activation showed high regioselectivity for the most acidic C—H bond. The oxazoles were converted cleanly to the corresponding C2 carboxylic acids (see Table 2 below, entries 3a-3c). It is interesting to note that these substrates react selectively at the C3 position when traditional acylation methodologies are employed.[9]

Carboxylation of the related thiazoles afforded comparable selectivities; parent thiazole gave a 2.3/1 mixture of C2/C5 regioisomers, attributed to the presence of similarly acidic protons in these positions (Table 2, entries 3d-3f). The azoles (3g,3h) and pyrimidine (3i) were not activated by [(IPr)AuOH] as all C—H bonds have a $pKa_{DMSO}$ exceeding 30.3, however the more basic [(ItBu)AuOH] (ItBu=1,3-di-tert-butylimidazol-2-ylidene) species (pKa=32.4) could catalyze their carboxylation (Table 2, entries 3g-3i). Substrates containing three or four heteroatoms were also converted to their corresponding carboxylic acids with high regio-selectivity (Table 2, entries 3j-3l).

TABLE 2

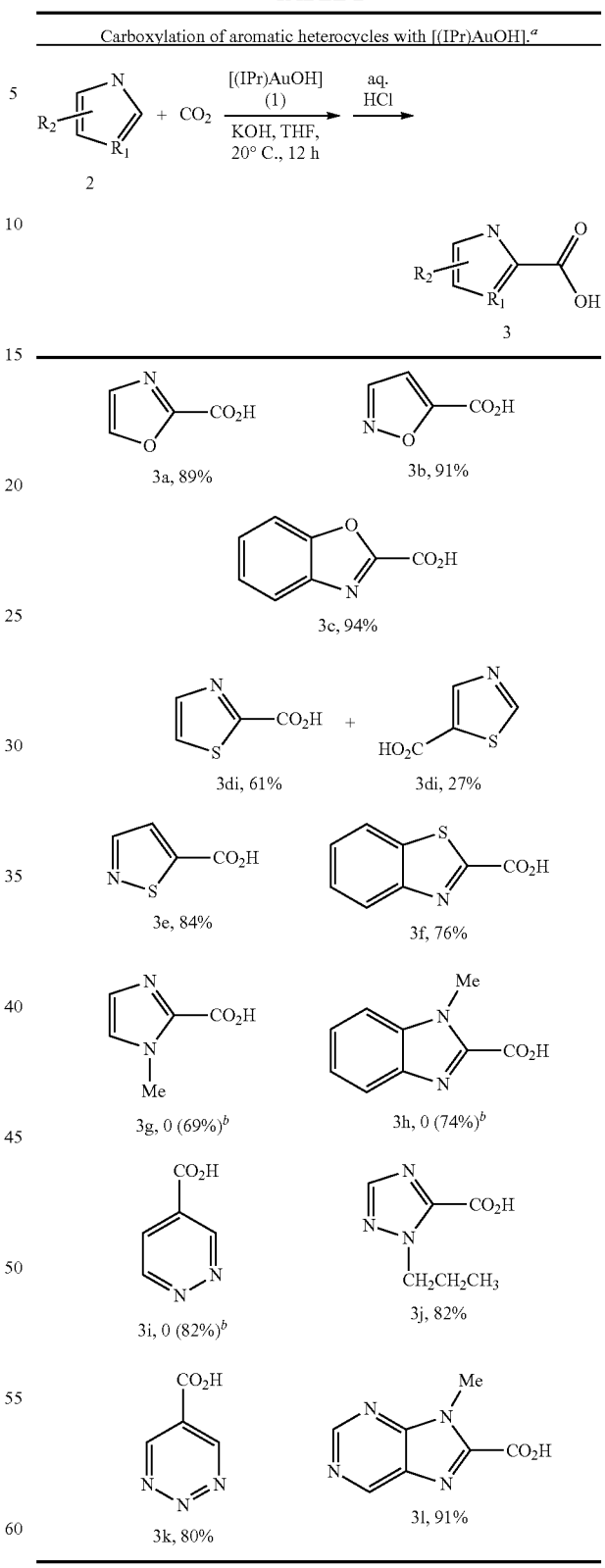

Carboxylation of aromatic heterocycles with [(IPr)AuOH].[a]

[a]Yields are isolated and average of two runs.
[b]Reaction performed using [(I$^t$Bu)AuOH].

Synthetic methodology often necessitates the conversion of carboxylic acid to ester. This could be achieved by reaction with an appropriate alkyl halide. Thus following this carboxylation protocol, the potassium carboxylate salts of 3a-3c and 3e-3f were quenched with iodomethane to afford the corresponding methyl esters 4a-4c and 4e-4f in good isolated yields (>80%) [Not shown in Table 2 but with corresponding structures—i.e. 4a is the methyl ester of carboxylic acid 3a].

Table 3 below list results for the carboxylation of various arenes, in these examples halogen substituted benzene compounds using [(IPr)AuO H] (1) as an example complex.

Carboxylation Reactions—Copper Complexes

N-Carboxylation of 2-methylimidazole with [NHC-copper(I)] catalysts is shown in Table 4 below, wherein the initially formed carboxyl compound was converted to the methyl ester by quenching with methyl iodide as in the scheme below where [Cu] indicates a copper complex such as those listed in Table 4.

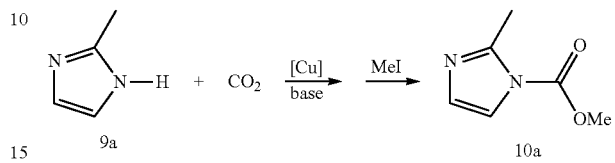

9a  →  10a

TABLE 3

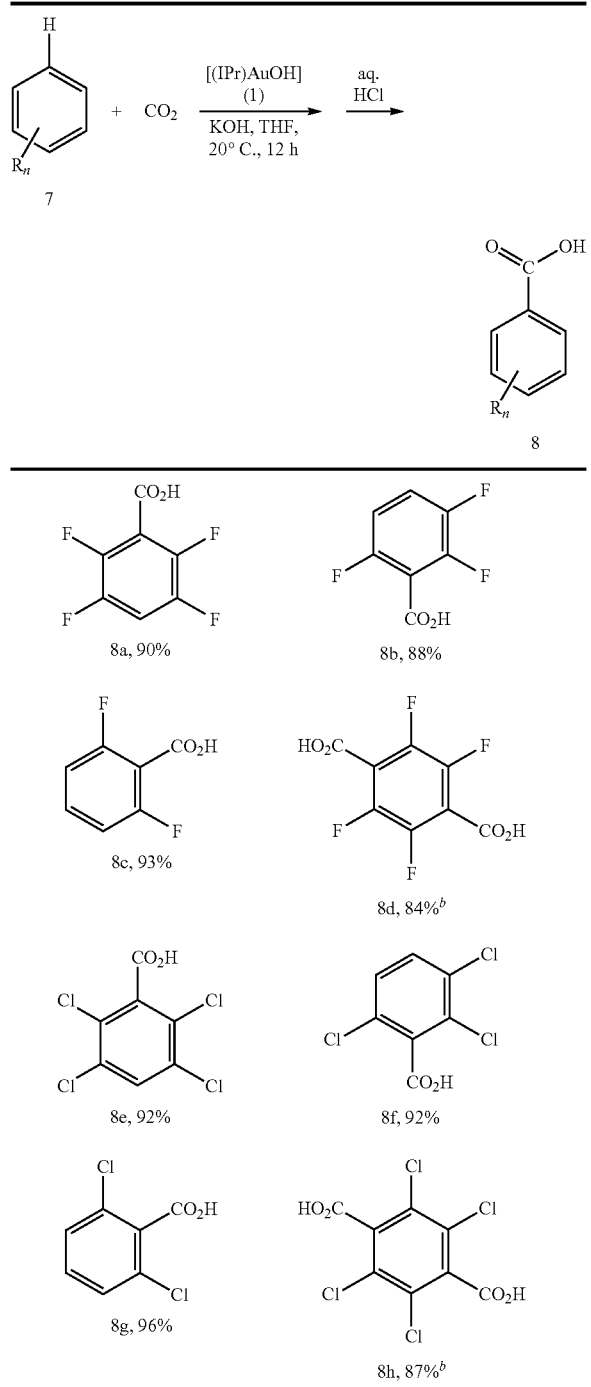

TABLE 4

| Entry | [Cu] | Loading (mol %) | Base | Solvent | Yield[b] (%) |
|---|---|---|---|---|---|
| 1 | [Cu(IpR)(OH)] | 0.5 | KOH | THF | 32 |
| 2 | [Cu(IPr)(OH)] | 1.5 | KOH | THF | 89 |
| 3 | [Cu(IPr)(OH)] | 3.0 | KOH | THF | 93 |
| 6 | [Cu(IPr)(OH)] | 3.0 | KOH | toluene | 78 |
| 7 | [Cu(IPr)(OH)] | 3.0 | KOH | Et$_2$O | 84 |
| 8 | [Cu(IPr)(OH)] | 3.0 | KOH | dioxane | 80 |
| 9 | [Cu(IPr)(OH)] | 3.0 | KOH | methanol | 65 |
| 10 | [Cu(IPr)Cl] | 1.5 | NaOH | THF | 72 |
| 11 | [Cu(IPr)Cl] | 1.5 | KOH | THF | 84 |
| 12 | [Cu(IPr)Cl] | 1.5 | CsOH | THF | 91 |
| 13 | [Cu(SIPr)Cl] | 1.5 | CsOH | THF | 82 |
| 14 | [Cu(IMes)Cl] | 1.5 | CsOH | THF | 16 |
| 15 | [Cu(SIMes)Cl] | 1.5 | CsOH | THF | 23 |

[a]Conditions: 1 mmol 2a, 1.1 mmol base, pCO$_2$ = 1.5 bar, 40° C., 20 Hz, 5 mL solvent, t = 8 h.
[b]Isolated yield.

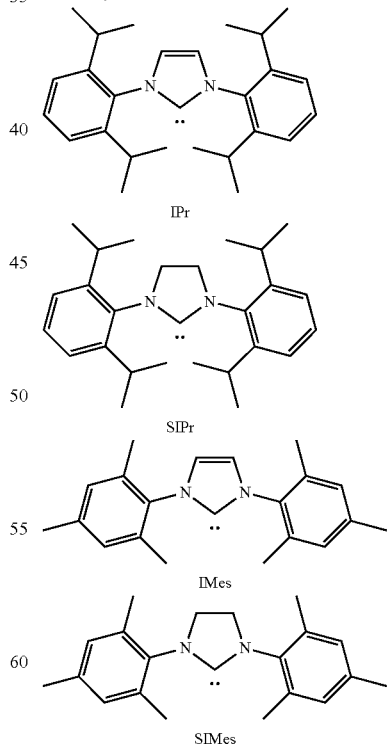

[a]Yields are isolated and average of two runs.
[b]Reaction performed using 2 equivalents of KOH.

As with gold examples above, the copper complex catalyst can be generated in situ by the reaction of a chloride complex with a hydroxide base (entries 10 to 15). It is worth noting that the use of alternative NHC ligands gave lower yields of 10a under analogous reaction conditions (Table 4, entries 13-15).

Copper complexes were used to carboxylate an N—H bond of a variety of heterocycles using the optimised conditions found from the work listed above in Table 4 using 1.5 to 3 mol % catalyst. The results are given in Table 5 below, where the pKa of the H at the site of reaction is indicated on the structure of each substrate 9.

The imidazole, indole and pyrazole derivatives were transformed cleanly and quantitatively to the corresponding methyl esters (Table 5, entries 1-3). Competitive O— and C— reactivity has been reported to render the carbamoylation of indolinones and pyrrolones problematic.[10] However with the copper hydroxide complex [Cu(IPr)(OH)] highly regioselective N-carboxylation of 9e was achieved albeit with a comparatively low yield (Table 5, entry 4).

TABLE 5

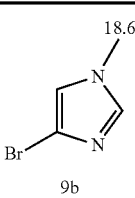

| Entry | Substrate | Yield (%)[a] | TOF (h$^{-1}$)[b] |
|---|---|---|---|
| 1 | 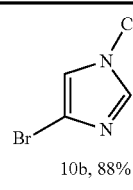 9b | 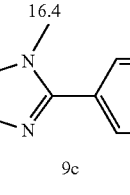 10b, 88% | 17.5 |
| 2 | 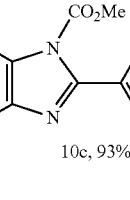 9c | 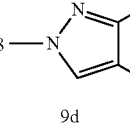 10c, 93% | 19.1 |
| 3 | 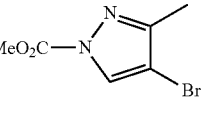 9d | 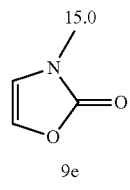 10d, 85% | 16.6 |
| 4 | 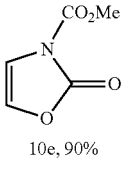 9e | 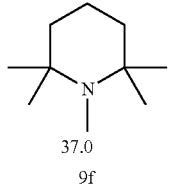 10e, 90% | 20.3 |
| 5 | 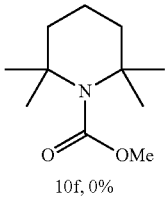 9f | 10f, 0% | 0 |
| 6 | 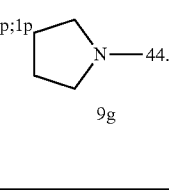 9g | 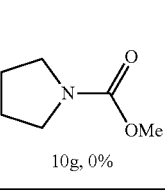 10g, 0% | 0 |

[a]Yields are isolated and the average of three runs.
[b]Turnover frequency determined after 1 hour, defined as mol of ester per mol of Cu per hour.

Catalyst activity can be correlated with the acidity of the N—H bond ($r^2=0.9989$), which supports a rate-limiting N—H activation step. [Cu(IPr)(OH)] (IPr=1,3-bis(diisopropyl)phenylimidazol-2-ylidene) has a $pKa_{DMSO}$ of 27.7(2) by potentiometric titrimetry and so is expected to carboxylate C—H or N—H bonds with a lower pKa. As predicted from their high pKa values, 9f and 9g were not activated and no product was detected(Table 5, entries 5 and 6).

Carboxylation of C—H bonds by copper catalysts is exemplified in Table 6 below where the pKa of the H at the site of reaction is indicated on the structure of each substrate 11.

Conversion of heteroaromatics 11a-11c gave only 16-29% NMR yield of the corresponding methyl esters when the reaction was carried out at 40° C., Simply increasing reaction temperature to 65° C. significantly improved catalyst turnover to afford 12a-12c in high yields (as shown in Table 6, entries 1-3). For 12c, this pathway is distinct from the conventional Friedel-Crafts mechanism, which promotes C3-selectivity.[11] Polyfluorinated arenes 11d-11e underwent smooth conversion to 12d-12e under analogous reaction conditions (Table 6, entries 4 and 5). Additionally, the presence of two activated C—H bonds in 11e allowed facile synthesis of the symmetrical terephthalic ester 12f when 2.2 eq of CsOH were employed.

TABLE 6

C-Carboxylation of aromatics with [Cu(IPr)OH].

| Entry | Substrate | Yield (%)[a] |
|---|---|---|
| 1 | 11a (24.8) | 12a, 90% |
| 2 | 11b (27.3) | 12b, 82% |
| 3 | 11c (27.7) | 12c, 77% |
| 4 | 11d (26.1) | 12d, 85% |
| 5 | 11e (23.1) | 12e, 93% |
| 6 | 11e (23.1) | 12f, 80%[b] |

[a]Yields are isolated and the average of three runs.
[b]Using 2.2 eq of CsOH.

TABLE 7

Formation of complexes via decarboxylation reactions

Ar—COOH + Au(IPr)OH →(Δ, toluene 110° C.) Z—Au—Ar + CO$_2$ + H$_2$O
(19a-19l)

19a (2 h, 99%)[a]

19b (2 h, 98%)[a]

TABLE 7-continued

Formation of complexes via decarboxylation reactions $$Ar-COOH + Au(IPr)OH \xrightarrow[\text{toluene } 110°C]{\Delta} Z-Au-Ar + CO_2 + H_2O$$
19a-19l 19c (6 h, 96%)[a] — OMe substituted 19d (1 h, 99%)[a] — NMe₂ substituted 19e (2 h, 99%)[a] — 2,6-diF substituted 19f (20 h, 97%)[a] — 2-F substituted 19g (6 h, 96%)[a] — pentafluoro substituted 19h (24 h, 99%)[b] — CN substituted 19i (25 h, 55%)[c] — NO₂ substituted 19j (20 h, 95%)[b,c] — CHO substituted 19k (20 h, >99%)[b] — styryl Au(IPr)

19l (70 h, 95%)[b,c] — 4-MeO substituted

Reaction conditions: 0.033 mmol [Au(IPr)(OH)], 0.033 mmol carboxylic acid, 0.4 mL toluene, 110° C.
[a]Isolated yields.
[b]120° C.
[c]NMR yield using mesitylene as internal standard.

A wide range of carboxylic acids may be employed in the method. Even relatively unactivated compounds such as p-methoxybenzoic acid can give high yields (resulting in 19l).

The reaction is applicable to heteroaromatic complexes as well. The products in Table 8 (below) were made from the corresponding carboxylic acids using the same conditions as in Table 7.

TABLE 8

20a (0.5 h, >99%)[a] — furan-2-yl Au(IPr)

20b (2 h, 96%)[a] — thiophen-2-yl Au(IPr)

20c (0.5 h, >99%)[a] — oxazol-5-yl Au(IPr)

20d (2 h, >99%)[a] — benzofuran-2-yl Au(IPr)

20e (2 h, 98%)[a] — benzothiophen-2-yl Au(IPr)

The adducts shown above in Tables 7 and 8 may be recarboxylated with $CO_2$, for example isotopically labeled $CO_2$ to form complexes of the form $Z-M-OOC-R^x$. Yields may be of the order of 60% or more. The carboxylic acids may then be regenerated from the metal complexes in accordance with the procedure illustrated in Scheme 4.

REFERENCES (1) (a) Aresta, M. Carbon Dioxide Recovery and Utilisation. Kluwer Academic. Dordrecht, The Netherlands, 2003. (b) Sakakura, T.; Choi, J. C.; Yasuda, H, Chem. Rev. 2007, 107, 2365. (c) Jessop, P. G.; Joó, F.; Tai, C. C. Coord. Chem. Rev. 2004, 248, 2425.

(2) For $CO_2$ Coupling with allyl halides: (a) Franks, R. J.; Nicholas, K. M. Organometallics 2009, 19, 1458. (b) Johansson, R.; Wendt, O. F. Dalton Trans. 2007, 488.

(3) For $CO_2$ coupling with alkenes: (a) Takimoto, M.; Nakamura, Y.; Kumura, K.; Mori, M. J. Am. Chem. Soc, 2004, 126, 5956. (b) Papai, I.; Schubert, G.; Mayer, I.; Besenyei, G.; Aresta, M. Organometallics 2004, 23, 5252.

(4) For $CO_2$ coupling with alkynes and allenes: (a) Saito, S.; Nakagawa, S.; Koizumi, T.; Hirayama, K.; Yamamoto, Y. J. Org. Chem. 1999, 64, 3975. (b) Aoki, M.; Kaneko, M.; Izumi, S.; Ukai, K.; lwasawa, N. Chem. Commun. 2004, 2568. (c) North, M. Angew. Chem., Int. Ed. 2009, 48, 4104.

(5) For recent examples of metal-catalyzed carboxylation involving $CO_2$ and an organometallic reagent see: (a) Ukai, K.; Aoki, M.; Takaya, J.; lwasawa, N. J. Am. Chem. Soc. 2006, 128, 8706. (b) Yeung, C. S.; Dong, V. M. J. Am. Chem. Soc. 2008, 130, 7826. (c) Corea, A.; Martin, R. J. Am. Chem. Soc. 2009, 131, 15974.

(6) "A N-Heterocyclic Carbene Gold Hydroxide Complex: A Golden Synthon" Gaillard, S.; Slawin, A. M. Z.; Nolan, S. P. Chem. Commun. 2010, 46, 2742-2744.

(7) Jurkauskas, V.; Sadighi, J. P.; Buchwald, S. L. Conjugated Reduction of α,β-Unsaturated Carbonyl Compounds Catalyzed by a Copper Carbene Complex. Org. Lett. 2003, 5, 2417-2420.

(8) Kaur, H.; Zinn, F. K.; Stevens, E. D.; Nolan, S. P. (NHC) CuI (NHC=N-Heterocyclic Carbene) Complexes as Efficient Catalysts for the Reduction of Carbonyl Compounds. Organometallics 2004, 23, 1157-1160.

(9) (a) Park, C. M.; Kim, S. Y.; Park, W. K.; Park, N. S.; Seong, C. M. Bioorg. Med. Chem. Lett. 2008, 18, 3844. (b) Nemoto, K.; Onozawa, S., Egusa, N.; Morohashi, N.; Hattori, T. Tetrahedron Lett. 2009, 50, 4512. (c) Olah, G. A.;

Török, B.; Joschek, J. P.; Bucsi, I.; Esteves, P. M.; Rasul, G.; Prakash, G. K. S. *J. Am. Chem. Soc.* 2002, 124, 11379, and references cited therein.

(10) (a) Rajeswaran, W. G.; Cohen, L. A. *Tetrahedron* 1998, 54, 11375-11380. (b) Hamashima, Y.; Suzuki, T.; Takano, H.; Shimura, Y.; Sedeoka, M. *J. Am. Chem. Soc.* 2005, 127, 10164-10165.

(11) (a) Park, C. M.; Kim, S. Y.; Park, W. K.; Park, N. S.; Seong, C. M. *Bioorg. Med. Chem. Lett.* 2008, 18, 3844-3847. (b) Nemoto, K.; Onozawa, S.; Egusa, N.; Morohashi, N.; Hattori, T. *Tet. Lett.* 2009, 50, 4512-4514.

(12) N. P. Mankad, T. G. Gray, D. S. Laitar, J. P. Sadighi, *Organometallics* 2004, 23, 1191.

(13) A. Bonet, V. Lillo, J. Ramirez, M. M. Diaz-Requejo, E. Fernández, *Org. Biomol. Chem.* 2009, 7, 1533.

(14) de Frémont, P.; Scott, N. M.; Stevens, E. D.; Ramnial, T.; Lightbody, O. C.; Macdonald, C. L. B.; Clyburne, J. A. C.; Abernethy, C. D.; Nolan, S. P. Synthesis of Well-Defined N-Heterocyclic Carbene Silver (I) Complexes. Organometallics, 2005, 24, 6301-6309.

(15) Dupuy, S.; Lazreg, F.; Slawin, A. M. Z.; Cazin, C. S. J.; Nolan, S. P. *Chem. Commun.* 2011, 47, 5455-5457.

The invention claimed is:

1. A method of carboxylation, the method comprising:
   contacting a complex of the form Z-M-OR, wherein the group Z is a nitrogen containing heterocyclic carbine, where
   M is copper, silver or gold, and —OR is selected from the group consisting of OH, alkoxy and aryloxy;
   wherein the nitrogen containing heterocyclic carbene ligand is of the form:

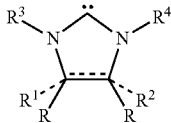

wherein each of the groups R, $R^1$ $R^2$, $R^3$ and $R^4$ are the same or different, and the dashed line in the ring represents optional unsaturation with $R^1$ and $R^2$ absent;
   wherein each R and $R^1$, $R^2$, $R^3$ and $R^4$ are, independently for each occurrence, selected from: H, a primary or secondary alkyl group; unsaturated alkyl, alkyl-substituted, or unsubstituted phenyl; alkyl-substituted or unsubstituted naphthyl; alky-substituted or unsubstituted anthracenyl; or alkyl-substituted or unsubstituted heterocyclic aromatic rings;
   or
   wherein the nitrogen containing heterocyclic carbene ligand is from one of the formulas I, II, III, or IV:

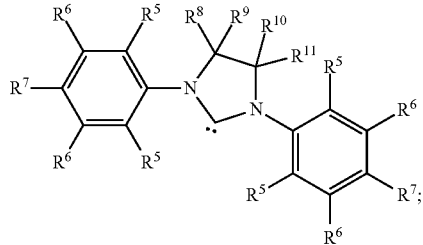

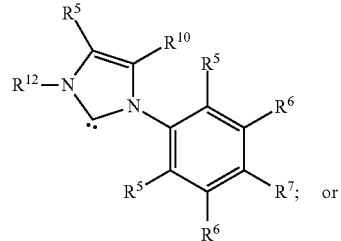

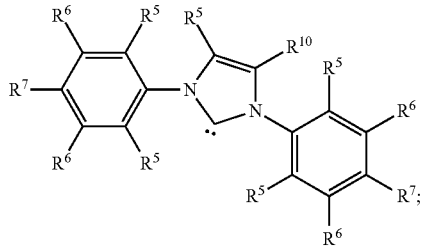

wherein each group $R^5$, $R^6$ and $R^7$, is independently for each occurrence selected from: H; a primary or secondary alkyl group; alkyl-substituted or unsubstituted phenyl; alkyl-substituted or unsubstituted naphthyl; or alkyl-substituted or unsubstituted anthracenyl;
   wherein $R^8$, $R^9$, $R^{10}$ and $R^{11}$ are each independently for each occurrence H; a primary or secondary alkyl group; alkyl-substituted or unsubstituted aryl; or in formulas (II) and (IV) together with the carbons carrying them form a fused 4-8 membered carbocylic ring or a fused aromatic ring; and
   wherein $R^{12}$ is alkyl or a cycloalkyl;
   with
   a reactant comprising an alkyl-substituted, halo-substituted, or unsubstituted aromatic compound; an alkyl-substituted, halo-substituted, or unsubstituted heteroaromatic compound; or an alkyl-substituted, halo-substituted, or unsubstituted heterocyclic compound;
   the reactant comprising a C—H or a N—H bond capable of carboxylation; and
   a source of $CO_2$.

2. The method according to claim 1, wherein the pKa of the C—H or the N—H bond of the reactant is lower than that of the complex Z-M-OR.

3. The method according to claim 1, wherein the carboxylation is carried out in the presence of a base.

4. The method according to claim 3, wherein the base is an alkali metal hydroxide or alkoxide.

5. The method according to claim 1, wherein the nitrogen containing heterocyclic carbene ligand Z is selected from the group consisting of:

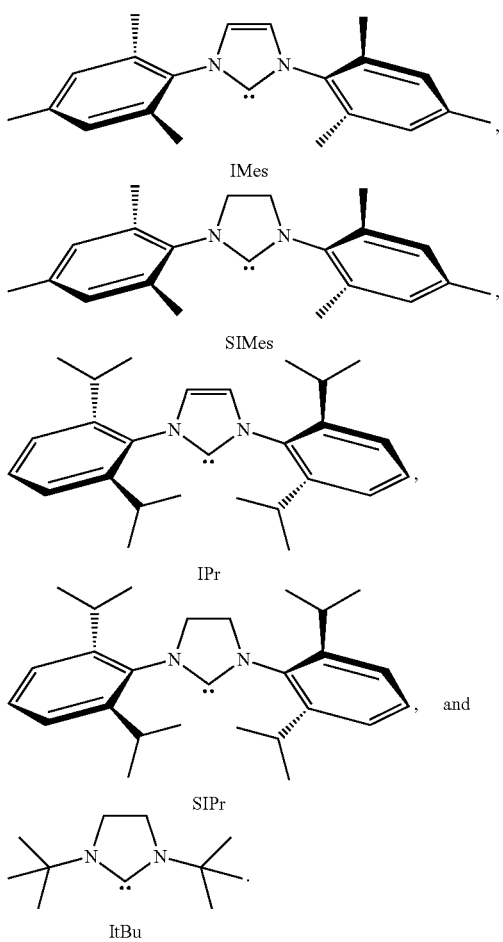

6. The method according to claim 5, wherein the complex is selected from the group consisting of: [M(OH)(IMes)], [M(OH)(SIMes)], [M(OH)(IPr)], [M(OH)(ItBu)J], and [M(OH)(SIPr)], where M is Au, Ag or Cu.

7. The method according to claim 1, wherein the complex of the form Z-M-OR is formed in situ from a complex of the form Z-M-X or from a salt of the form Z-M$^+$X$^-$ wherein X is a leaving group of an anionic ligand or an anion.

8. The method according to claim 7, wherein the leaving group X is selected from the group consisting of halide, carboxylate, alkylsulfonate, acetate, trifluoroacetate, tetrafluroborate, hexafluorophosphate, hexafluoroantimonate, cyanide, thiocyanates, isothiocyanates, cyanates, isocyanates, azides and selenocyanates.

9. The method according to claim 1, wherein the primary or secondary alkyl group is $C_1$-$C_{10}$.

10. A method of carboxylation, the method comprising;
contacting a complex of the form Z-M-OR, wherein the group Z is a nitrogen containing heterocyclic carbine; where
M is copper, silver or gold, and —OR is selected from the group consisting of OH, alkoxy and aryloxy;
wherein the nitrogen containing heterocyclic carbene ligand is of the form:

wherein each of the groups R and R$^1$, are the same or different, and the dashed line in the ring represents optional unsaturation with R$^1$ absent;
wherein each R and R$^1$ are, independently for each occurrence, selected from: H, a primary or secondary alkyl group; alkyl-substituted, or unsubstituted phenyl; alkyl-substituted or unsubstituted naphthyl; alky-substituted or unsubstituted anthracenyl; or alkyl-substituted or unsubstituted heterocyclic aromatic rings;
with
a reactant comprising an alkyl-substituted, halo-substituted, or unsubstituted aromatic compound; an alkyl-substituted, halo-substituted, or unsubstituted heteroaromatic compound; or an alkyl-substituted, halo-substituted, or unsubstituted heterocyclic compound;
the reactant comprising a C—H or a N—H bond capable of carboxylation; and
a source of $CO_2$.

11. The method according to claim 10, wherein the pKa of the C—H or the N—H bond of the reactant is lower than that of the complex Z-M-OR.

12. The method according to claim 10, wherein the carboxylation is carried out in the presence of a base.

13. The method according to claim 12, wherein the base is an alkali metal hydroxide or alkoxide.

14. The method according to claim 10, wherein the complex of the form Z-M-OR is formed in situ from a complex of the form Z-M-X or from a salt of the form Z-M$^+$X$^-$ wherein X is a leaving group of an anionic ligand or an anion.

15. The method according to claim 7, wherein the leaving group X is selected from the group consisting of halide, carboxylate, alkylsulfonate, acetate, trifluoroacetate, tetrafluroborate, hexafluorophosphate, hexafluoroantimonate, cyanide, thiocyanates, isothiocyanates, cyanates, isocyanates, azides and selenocyanates.

16. The method according to claim 10, wherein the primary or secondary alkyl group is $C_1$-$C_{10}$.

* * * * *

UNITED STATES PATENT AND TRADEMARK OFFICE
CERTIFICATE OF CORRECTION

PATENT NO. : 9,120,711 B2
APPLICATION NO. : 13/702886
DATED : September 1, 2015
INVENTOR(S) : Steven P. Nolan and Catherine Cazin It is certified that error appears in the above-identified patent and that said Letters Patent is hereby corrected as shown below:

IN THE CLAIMS:

In column 25, claim 1, please change line 27 to:

"group Z is a nitrogen containing heterocyclic carbene"

In column 26, claim 1, please change formula III to:

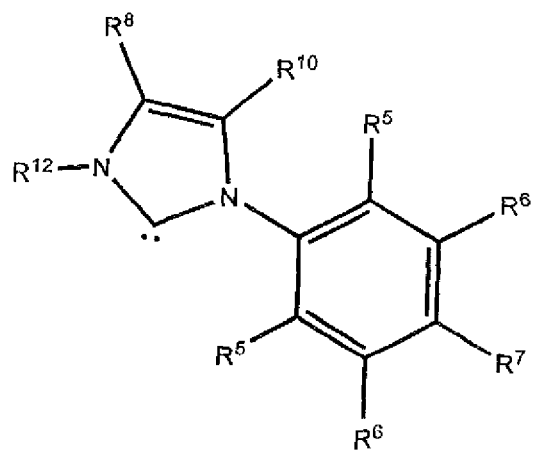

Signed and Sealed this
Twenty-ninth Day of March, 2016

Michelle K. Lee
*Director of the United States Patent and Trademark Office*

CERTIFICATE OF CORRECTION (continued)
U.S. Pat. No. 9,120,711 B2

IN THE CLAIMS:

In column 26, claim 1, please change formula IV to:

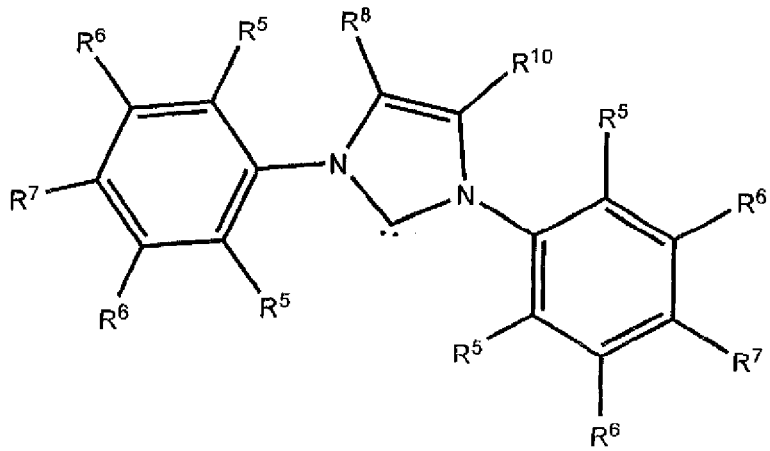

In column 27, claim 6, please change line 40 to:

"[M(OH)(SIMes)], [M(OH)(IPr)], [M(OH)(ItBu)], and"

In column 28, claim 10, please change line 3 to:

"group Z is a nitrogen containing heterocyclic carbene"

In column 28, claim 15, please change line 46 to:

"15. The method according to claim 14, wherein the leaving"